United States Patent
Shapiro-Ilan et al.

(10) Patent No.: US 7,374,773 B1
(45) Date of Patent: May 20, 2008

(54) APPLICATION OF ENTOMOPATHOGENIC NEMATODE-INFECTED CADAVARS FROM HARD-BODIED ARTHROPODS FOR INSECT SUPPRESSION

(75) Inventors: David I. Shapiro-Ilan, Macon, GA (US); W. Louis Tedders, Perry, GA (US); Edwin E. Lewis, Blacksburg, VA (US)

(73) Assignees: The United States as represented by the Secretary of Agriculture, Washington, DC (US); Virginia Polytechnic Institute and State University, Blacksburg, VA (US); Virginia Tech Intellectual Properties, Inc., Blacksburg, VA (US)

( * ) Notice: Subject to any disclaimer, the term of this patent is extended or adjusted under 35 U.S.C. 154(b) by 792 days.

(21) Appl. No.: 10/726,479

(22) Filed: Dec. 4, 2003

(51) Int. Cl.
*A01N 25/32* (2006.01)
(52) U.S. Cl. .......................... 424/406; 119/6.7; 424/84; 424/265.1; 424/405; 424/410; 424/538
(58) Field of Classification Search ...... 424/93.1–93.6; 435/177–179, 235.1, 243, 252.1–258.4, 260, 435/348
See application file for complete search history.

(56) References Cited

U.S. PATENT DOCUMENTS

| | | | | |
|---|---|---|---|---|
| 5,165,930 A | * | 11/1992 | Smart et al. | 424/93.1 |
| 6,261,553 B1 | * | 7/2001 | Bradley et al. | 424/93.5 |
| 6,280,723 B2 | * | 8/2001 | Stimac et al. | 424/93.5 |
| 6,474,259 B1 | | 11/2002 | Gaugler | 119/6.7 |
| 6,524,601 B1 | * | 2/2003 | Shapiro et al. | 424/405 |

OTHER PUBLICATIONS

Shapiro-Ilan, D.I. et al., "Formulation of Entomopathogenic Nematode-Infected Cadavers", *J. Invertebrate Pathology*, vol. 78, pp. 17-23, 2001.
Shapiro, D.I., et al., "Comparison of Entomopathogenic Nematode Infectivity from Infected Hosts Versus Aqueous Suspension", *Environmental Entomology*, vol. 28(5), pp. 907-911, Oct. 1999.
Shapiro, D.I., et al., "Susceptibility of Diaprepes Abbreviatus (Coleoptera: Curculionidae) Larvae to Different Rates of Entomopathogenic Nematodes in the Greenhouse", *Florida Entomologist*, vol. 83(1), pp. 1-9, Mar. 2000.
Jansson, R.K., et al., "Field Efficacy and Persistence of Entomopathogenic Nematodes (Rhabditida: Steinernematidae, Heterorhabditidae) for Control of Sweetpotato Weevil (Coleoptera: Apionidae) in Southern Florida", *J. Economic Entomology*, vol. 86(4), pp. 1055-1063, Aug. 1993.
Parkman, J.P., et al., "Establishment and Persistence of *Steinernema scapterisci* (Rhabditida: Steinernematidae) in Field Populations of *Scapteriscus* spp. Mole Crickets (Orthoptera: Gryllotalpidae)", *J. Entomol. Sci.*, vol. 28(2), pp. 182-190, 1993.
Shapiro, D.I., et al., "Comparison of Entomopathogenic Nematode Dispersal from Infected Hosts Versus Aqueous Suspension", *Environmental Entomology*, vol. 25(6), pp. 1455-1461, Dec. 1996.
Welch, H.E., et al., "Field Experiement on the Use of a Nematode for the Control of Vegetable Crop Insects", *Proc. Entomol. Soc. Ontario*, vol. 91, pp. 197-202, 1960.

(Continued)

*Primary Examiner*—Neil S. Levy
(74) *Attorney, Agent, or Firm*—John Fado; Gail E. Poulos

(57) ABSTRACT

Pesticidal and/or antimicrobial biological agent-infected hard-bodied arthropod cadavers, such as from the family Tenebrionidae are used to control pest and/or microbial infestations in agriculture, commercial and urban environments.

4 Claims, 4 Drawing Sheets

OTHER PUBLICATIONS

Creighton, C.S., et al., "*Heterorhabditis* sp. (Nematoda: Heterorhabditidae): A Nematode Parasite Isolated from the Banded Cucumber Beetle *Diabrotica balteata*", *J. Nematology*, vol. 17(2), pp. 150-153, 1985.

Jansson, R.K., et al., "Application Methods for Entomopathogenic Nematodes (Rhabditida: Heterorhabkitidae): Aqueous Suspension Versus Infected Cadavers", *Florida Entomologist*, vol. 77(2), pp. 281-284, Jun. 1994.

Wilson, M.J., et al., "Laboratory Tests of the Potential of Entomopathogenic Nematodes for the Control of Field Slugs (*Deroceras reticulatum*)", *J. Invertebrate Pathology*, vol. 64, pp. 182-187, 1994.

Shapiro-Ilan, D.I., et al., "Factors Affecting Commercial Success: Case Studies in cotton, Turf and Citrus", *IN: Entomopathogenic Nematology*, R. Gaugler, Ed., pp. 333-356, 2002, CABI, New York, NY.

Shapiro-Ilan, D.I., et al., "Formulation of Entopathogenic Nematode-Infected Cadavers", *J. Invertebrate Pathology*, vol. 78, pp. 17-23, 2001.

Shapiro-Ilan, D.I., et al., "Superior Efficacy Observed in Entomopathogenic Nematodes Applied in Infected-Host Cadavers Compared with Application in Aqueous Suspension", *J. Invertebr. Pathol.*, vol. 83, pp. 270-272, 2003.

Shapiro-Ilan, D.I., et al., "Production Technology for Entomopathogenic Nematodes and their Bacterial Symbionts", *J. Industrial Microbiology*, vol. 28, pp. 137-146, 2002.

Rueda, L.M., et al., "Natural Occurrence of Entomogenous Nematodes in Tennessee Nursery Soils", *J. Nematology*, vol. 25(2), pp. 181-188, 1993.

* cited by examiner

APPLICATION OF ENTOMOPATHOGENIC NEMATODE-INFECTED CADAVARS FROM HARD-BODIED ARTHROPODS FOR INSECT SUPPRESSION

BACKGROUND OF THE INVENTION

1. Field of the Invention

This invention relates to compositions for preparing formulated hard-bodied arthropod cadavers, such as, for example, from the family Tenebrionidae such as *Tenebrio molitor*, containing biological organisms having pesticidal and/or antimicrobial activity; compositions containing formulated hard-bodied arthropod cadavers; and methods for preparing and using formulated arthropod cadavers.

2. Description of the Related Art

Control of pest and/or microbial infestations and the direct loss caused by infestations are costly. Myriad approaches have been pursued to control pests. Various pathogenic biological control agents such as species of nematodes, fungi, bacteria, virus, or protozoa can suppress populations of important pests. These biological control organisms are most often applied in aqueous suspension for control of agricultural pests. Their usage is limited by cost and, or inconsistent levels of efficacy in pest supression following field applications.

Entomopathogenic nematodes are just one example of a biocontrol agent which can be formulated into a carrier to control pests. Entomopathogenic nematodes in the genera *Steinernema* and *Heterorhabditis* are obligate parasites of insects which can control a wide variety of economically important pests. These nematodes are commercially applied as infective juveniles in aqueous suspension using various agricultural spray equipment, irrigation systems, or injection techniques (Grewal, Entomopathogenic nematology, Gaugler et al. (Eds), CABI, New York, N.Y., 265-288, 2002; Georgis, Formulation and Application Technology, IN: "Entomopathogenic Nematodes in Biological Control, supra, 173-194, 1990; Koppenhofer, Nematodes, IN: "Field Manual of Techniques in Invertebrate Pathology", L. A. Lacey and H. K. Kaya, Eds., 283-301, 200, Kluwer Academic Publishers, Dordrecht). Entomopathogenic nematodes generally infect their host by entering natural openings in the host. Heterorhabditids also have the ability to enter certain hosts through the cuticle using a tooth. After entering a host, symbiotic bacteria are released, the nematodes molt, reproduce, and after 1-3 generations, dauer stage juveniles emerge. The dauer juvenile stage is the only stage that is capable of surviving and infecting new hosts in the natural environment. Infective juveniles enter the host and release symbiotic bacteria which aid in (a) killing the host, (b) providing nutrients to the nematodes, and (c) releasing antibiotics, which prevent invasion by other microbes; the bacteria, however, cannot survive outside of the host in a natural environment (e.g. soil) without the nematode (Poiner, Biology and Taxonomy of *Steinemematidae* and *Heterorhabditidae*, In: Entomopathogenic Nematodes in Biological Control, R. Gaugler and H. K. Kaya, Eds., 23-62, 1990, CRC Press, Boca Raton, Fla.). The number of nematodes produced per insect varies among nematode species, and within species in different hosts. *Heterorhabditis bacteriophora* Poinar, for example, can produce over 50,000 infective juveniles per *Tenebrio molitar* larva (Shaprio-Ilan and Gaugler, Production Technology for Entomopathogenic Nematodes and Their Bacterial Symbionts, J. Ind. Microbiol. & Biotech., Volume 28, 137-146, 2002).

Entomopathogenic nematodes are important biological control agents for a variety of economically important pests in agricultural and urban environments (Grewal and Georgis, Entomophathogenic nematodes, IN: "Methods in Biotechnology", Volume 5, Biopesticides: Use and Delivery, F. R. Hall and J. J. Menn, Eds., 271-299, 1998, Totowa, N.J., Humana Press, Inc.; Kaya and Gaugler, Entomopathogenic Nematodes, Annu. Rev. Entomol., Volume 38, 181-206, 1993). The nematodes can be mass-produced using in vivo and in vitro methods (Friedman, Commercial production and development, IN: "Entomopathogenic Nematodes in Biological Control", R. Gaugler and H. K. Kaya, Eds., 153-172, 1990, Boca Raton, Fla., CRC Press; Sharpiro and Gaugler, 2002, supra). More wide-spread use of etnomopathogenic nematodes as biological control agents has been limited by cost competitiveness and inconsistent levels of field efficacy (Shapiro-Ilan et al., Factors Affecting Commercial Success: Case Studies in Cotton, Turf, and Citrus. IN: "Entomopathogenic Nematology", R. Gaugler, Ed., 333-356, 2002, CABI, New York, N.Y.).

Research indicates that entomopathogenic nematodes may also be applied in infected cadavers [(Creighton and Fasuliotis, Heterorhabditis sp. (Nematoda: Heterorhabditidae): A nematode parasite isolated from the banded cucumber beetle *Diabrotica balteata*, J. Nematology, Volume 17, 150-153, 1985; Jansson et al., Field efficacy and persistence of entomopathogenic nematodes (Rhabditida: Steinernematidae, Heterorhabditidae) for control of sweet potato weevil (Coleoptera: Apionidae) in Southern Florida, J. Econ. Entomology, Volume 86, 1055-1063, 1993)]. In this approach, nematode-infected cadavers are disseminated and pest suppression is subsequently achieved by the progeny infective juveniles that exit the cadavers. Laboratory studies indicate that nematode application in infected hosts may be superior to application in aqueous suspension (Shapiro and Glazer, Comparison of entomopathogenic nematode dispersal from infected hosts versus aqueous suspension, Environ. Entomol., Volume 25, 1455-1461, 1996; Shapiro and Lewis, Comparison of entomlopathogenic nematode infectivity from infected hosts versus aqueous suspension, Environ Entomol., Volume 28, 907-911, 1999). Indeed, experiments conducted in the greenhouse indicated superior pest suppression when nematodes were applied in infected-insect cadavers compared to aqueous applied nematodes (Shapiro-Ilan et al., Superior Efficacy Observed in Entomopathogenic Nematodes Applied in Infected-Host Cadavers Compared with Application in Aqueous Suspension, J. Invertebr. Pathol., Volume 83, 270-272, 2003). Additionally, for in vivo mass production, application of nematodes in infected cadavers can be less costly than aqueous application because it requires less steps in the process and is thus less costly (Shapiro-Ilan and Gauger, 2002, supra). Furthermore, Koppenhofer (2000, supra) reported that entomopathogenic nematodes can survive dry conditions for extended periods if they remain inside a host cadaver. Commercialization of nematode-infected cadavers has been prevented due to problems in storage and application (Koppenhofer, 2000, supra). Nematode-infected hosts stick together or rupture during transport and/or application, which results in reduced efficacy. Formulating nematode-infected cadavers by coating them can overcome problems of sticking or rupturing, and can provide shelf-life, stability and ease of handling (Shapiro-Ilan et al., U.S. Pat. No. 6,524,061, Feb. 25, 2003; Shapiro-Ilan et al., Formulation of Entomopathogenic Nematode-Infected Cadavers, J. Invertevr. Pathol., Volume 78, 17-23, 2001).

Various formulations for entomopathogenic organisms are known, however there remains a need in the art for nematode formulations which maintain infectivity and reproduction levels for effective biological control that requires the least amount of formulation and enhances the use of biocontrol agents thereby reducing reliance on chemical pesticides. The present invention, as described below, is different from related art nematode cadaver formulations.

SUMMARY OF THE INVENTION

It is therefore an object of the present invention to provide a hard-bodied arthropod cadaver formulation containing a pesticidal and/or antimicrobial biological organism as a biocontrol agent in which the cadavers resist sticking together and rupturing as compared to other arthropod cadavers.

A further object of the present invention is to provide a hard-bodied arthropod cadaver containing a pesticidal and/or antimicrobial biological organism as a biocontrol agent in which the percent survival of the pest organism is decreased as compared to aqueous formulations of conventionally prepared arthropod cadavers.

A still further object of the present invention is to provide *Tenebrionid* cadavers containing a pesticidal and/or antimicrobial biological organism as a biocontrol agent in which there is a resistance to sticking and rupturing as compared to other arthropod cadavers containing a pesticidal and/or antimicrobial biological organism as a biocontrol agent.

A still further object of the present invention is to provide *Tenebrio molitor* cadavers containing a pesticidal and/or antimicrobial biological organism as a biocontrol agent.

Another object of the present invention is to provide a biological control agent that includes a hard-bodied arthropod cadaver of the genus Tenebrio and a pesticidal and/or antimicrobial biological organism.

Another object of the present invention is to provide a method of biological control that includes the step of applying a hard-bodied arthropod cadaver containing a pesticidal and/or antimicrobial biological organism in amounts to at least reduce the levels of pest arthropods in an area infested with at least one type of pest arthropod.

A still further object of the present invention is to provide a method of biological control that includes the step of applying hard-bodied arthropods from the family Tenebrionidae containing a pesticidal and/or antimicrobial biological organism in amounts to at least reduce the levels of pest arthropods in an area infested with at least one type of pest arthropod.

Another object of the present invention is to provide a method of biological control that includes the step of applying *Tenebrio molitor* cadavers containing a pesticidal and/or antimicrobial biological organism in amounts to at least reduce the levels of pest arthropods in an area infested with at least one type of pest arthropod.

Further objects and advantages of the present invention will become apparent form the following description.

Figure 1A:
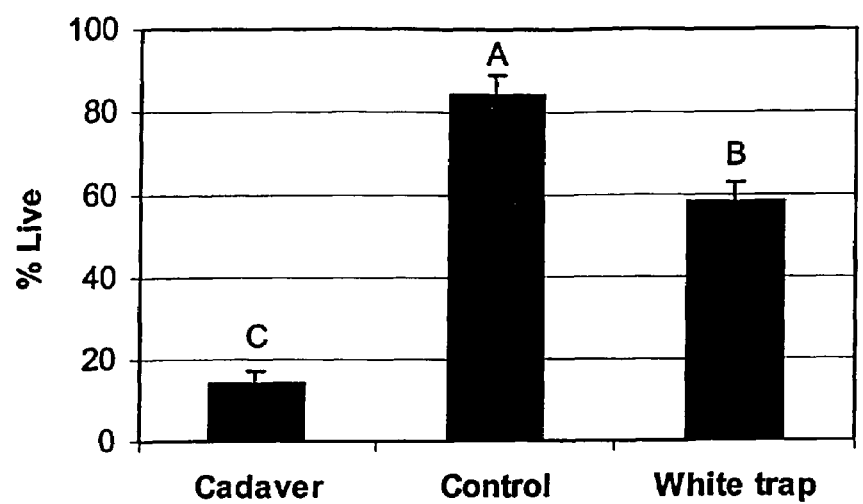
FIG. 1 is a graph showing mean percentage survival of *Diaprpepes abbreviatus* following application of *Heterorhabditis indica* (Hom 1 strain) in aqueous suspension (Form White traps or spray) or in infected *Tenebrio molitor* cadavers (A) 7, (B) 14, (C) 21, and (D) 28 days after nematode emergence began. Different letters above bars indicate statistical significance (Tukey's test).

FIG. 2 is a graph showing mean percentage survival of *Otiorhynchus sulcatus* following application of *Heterorhabditis bacteriophora* (Oswego strain) in aqueous suspension (From White traps) or in infected *Tenebrio molitor* cadavers (A) 7, (B) 14, and (C) 21 days after nematode emergence began. Different letters above bars indicate statistical significance (Tukey's test).

FIG. 3 is a graph showing the percent of cadavers ruptured or stuck together after four infected insects from *Tenebrio molitor* and *Galleria mellonella* (L.) were placed in petri dishes and shaken vigorously.

DETAILED DESCRIPTION OF THE INVENTION

The present invention is useful for providing entomopathogenic biological organisms for pesticidal and/or antimicrobial control of pests or disease in agricultural, commercial, and urban environments. Problems of cadaver rupture of sticking together can be overcome by using hard-bodied arthropod insect cadavers, such as, for example, those from the family Tenebrionidae, as the host arthropod which is the basis of the present invention. Using hard-bodied insects as the host arthropods to deter cadaver sticking and rupture is advantageous over formulating the cadavers with a coating because the former requires fewer steps in the process and thus is less costly. Various hard-bodied arthropods can be used as hosts in applying nematode infected-host cadavers, especially those arthropods that are amenable to mass production such as a number of insect larvae in the family Tenebrionidae, e.g., *T. molitor, Zophobas morio*, and the lesser mealworm *Alphitobius diaperinus*, as well as the house cricket *Acheta domesticus*; all of these insects are hosts of entomopathogenic nematodes (Rueda, et al., J. Nematol., Volume 25, 181-188, 1993; Wilson et al., J. Invertebr. Pathol., Volume 64, 182-187, 1994).

For purposes of the present invention, entomopathogenic biological organisms for pesticidal and/or antimicrobial control of pests include without limitation, bacteria, such as for example *Bacillus thuringensis*, fungi, such as for example, *Beauveria bassiana*; yeasts, viruses, such as for example, nucleopolyhedrovirus; microsporidians, protozoa, nematodes such as *Steinernema* or *Heterorhabditis* spp., and other lower organisms which are pathogenic toward target pests. Of course, any component or by product of the organism or stage of its life cycle which is infective to the host is considered to be within the scope of the invention. The term pesticidal and/or antimicrobial means that the biological organism is either pesticidal or antimicrobial and includes a biological organism which has both pesticidal and antimicrobial activity, such as for example, an entomopathogenic nematode.

The present invention provides pesticidal and/or antimicrobial biological organism-infected hard-bodied arthropod cadavers and methods of using the infected cadavers. The process for using pesticidal and/or antimicrobial biological organism-infected arthropod cadavers includes the steps of:

(a) infecting a hard-bodied arthropod cadaver with a pesticidal and/or antimicrobial biological organism to form an infected cadaver; and (b) applying a pest reducing amount of infected hard-bodied arthropod cadavers to an area to be treated.
Figure 1B:
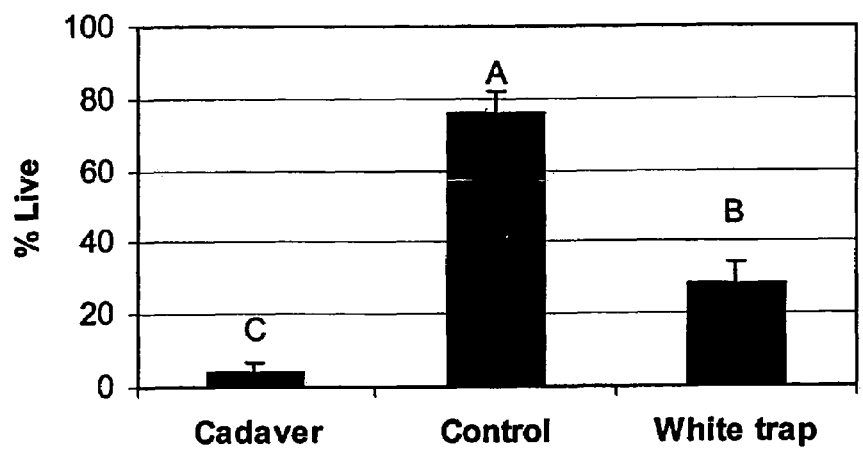
Figure 1C:
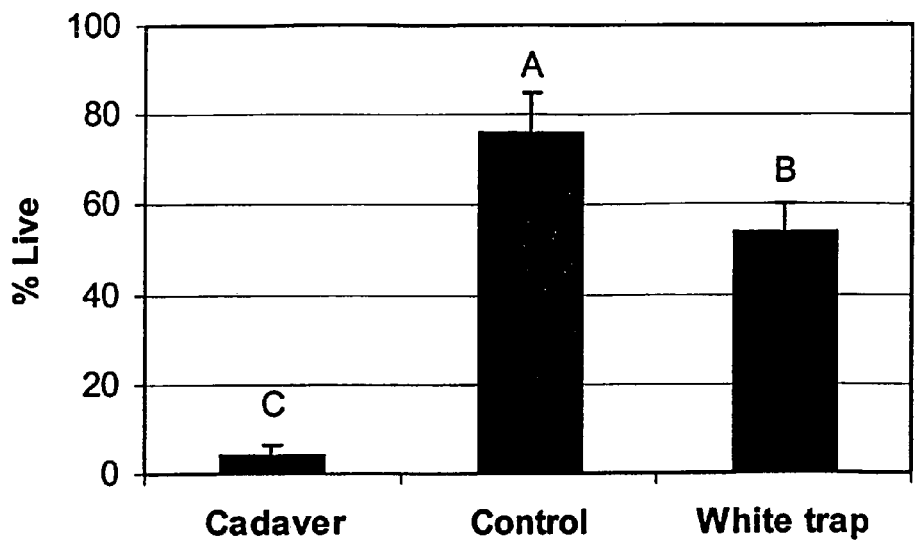
Figure 1D:
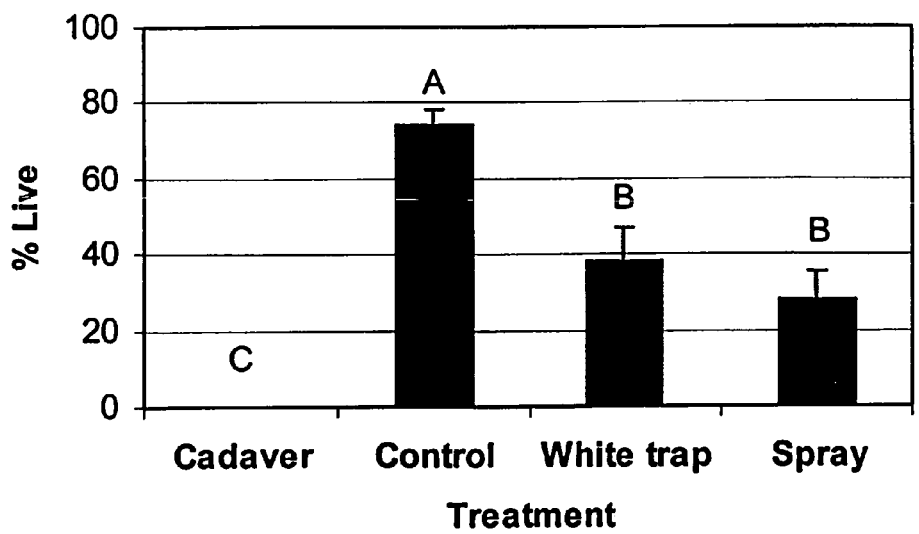

The target pests for control by means of the subject biological organism-infected hard-bodied arthropod cadavers include arthropods or other non-vertebrate pests in urban, commercial, or agricultural environments (Grewal and Georgis, 1998, supra; Koehler et al., Suceptability of cockroaches (Dictyoptera: Blatellidae, Blattidae) to infection by *Steinernema carpocapsae*, J. Econ. Entomol., Volume 35, 1184-1187, 1992; Weber et al., U.S. Pat. No. 5,172,514, 1992) or to supress microbial agents of agricultural or medical importance (Li and Webster, Bacterial symbionts of entomopathogenic nematodes-useful sources of bioactive materials, Canadian Chemical News, Volume 49, 15-16, 1997).

For purposes of the present invention, the term arthropod encompasses insects, arachnids, and crustaceans. The term hard-bodied arthropods includes any arthropod that has a hard exoskeleton that does not stick or rupture including, for example, insects in the family Tenebrionidae, e.g., *T. molitor*, *Zophobas morio*, and the lesser mealworm *Alphitobius diaperinus*, as well as the house cricket *Acheta domesticus*.

Nematode-infected hard-bodied arthropod cadavers are used with any entomopathogenic nematode infective juveniles. *Heterorhabditis bacteriophora* is a versatile nematode that has been marketed against a wide variety of economically important pests such as the black vine weevil, *Diaprepes* root weevil, and white grubs (Duncan et al., Entomopathogenic nematodes as a component of citrus root weevil IPM, IN: "Optimal Use of Insecticidal Nematodes in Pest Management", S. Polavarapu, Ed., 69-78, 1999, New Brunswick, N.J.: Rutgers University; Grewel and Georgis, Entomopathogenic nematodes, IN: "Methods in Biotechnology, Volume 5, Biopesticides: Use and Delivery, F. R. Hall and J. J. Menn, Eds., 271-299, 1998, Totowa, N.J.: Humana Press; Shapiro-Ilan et al., 2002, In: Entomopathogenic Nematology, supra). *Galleria mellonella*, a commonly used insect for in vivo mass production of entomopathogenic nematodes (Grewal and Georgis, 1998, supra) because it produces high nematode yields, is widely available commercially, and is very susceptible to infection (Woodring and Kaya, Steinernematid and Heterorhabditis Nematodes: A Handbook of Biology and Techniques, Southern California Cooperative Series Bulletin 331, Arkansas Agricultural Experimental Station, Fayetteville, Ark., 1998). *Tenebrio molitor* is also a common insect used in laboratory or commercial nematode production (Shapiro-Ilan and Gaugler, 2002, supra).

The following examples are intended only to further illustrate the invention and are not intended to limit the scope of the invention which is defined by the claims. *Tenebrio molitor* cadavers are used as a model system to illustrate the invention.

EXAMPLE 1

Insects were obtained from laboratory-reared cultures, and nematodes were reared in vivo according to Kaya and Stock (Manual of Techniques in Insect Pathology, Lacey, L. A. (Ed.), Academic Press, San Diego, Calif., 281-324, 1997). Nematode cultures, maintained on *Galleria mellonella* L., were used to inoculate the host insect for application; *Tenebrio molitor* L., *T. molitor* were infected on filter paper in Petri dishes (90 mm) weith about 600 (for *H. indica*) or about 800 (for *H. bacteriophora*) infective juveniles (Ijs) per insect. About seven days after inoculation, the infected *T. molitor* were transferred to a greenhouse. Two infected *T. molitor* were either placed directly on the soil of a 15-cm pot (the infected cadaver application), or on a White trap, which was adjacent to the corresponding pot designated for aqueous application. Thus, the nematode application rate was standardized to two nematode infected *Tenebrio molitor* worth of Ijs per pot. Previous studies indicated that the average (se) number of Ijs per *T. molitor* infected under similar conditions was about 58,250 (12,900) and 95,667 (9,765) for *H. indica* (Hom1) and *H. bacteriophora* (Owego), respectively (Shapiro-Ilan and Gaugler, J. Ind. Microbiol. & Biotech., Volume 28, 137-146, 2002)). The contents of White traps were poured into pots daily during the period of nematode emergence (up to about 23 days post-inoculation for the *D. abbreviatus* and about 21 days for *O. sulcatus*). Soil in each pot was kept at approximately the same moisture level throughout the experiment. Ambient and soil temperatures averaged (se) 26.8 (1.7) and 25.2 (1.1)° C. with *D. abbreviatus* and 23.7 (1.4) and 21.8 (0.8)° C. for *O. sulcatus*. For *D. abbreviatus*, each pot contained 5 target hosts (ca. $7^{th}$ and $9^{th}$ instar), and five baby carrots (ca. 5 cm long) for food. For *O. sulcatus*, each pot contained about 10 insects and one medium-sized carrot as a food source. The number of live insects remaining was determined 7,14,21, and 28 days after Ijs began to emerge with *D. abbreviatus*, i.e. 16,23,30, and 37 days post-inoculation; or 7,14, and 28 days after Ijs began to emerge with *O. sulcatus*. Pots for each sample date were organized separately in randomized block designs with 10 pots per treatment and a control (water only). With *D. abbreviatus*, an additional aqueous treatment was included consisting of nematodes harvested, stored, and sprayed onto soil in the pots in a manner similar to commercial production and how a grower might apply them. About twenty infected *T. molitor* intended for the spray treatment were inoculated in parallel with other treatments, maintained on White traps in the laboratory, which were harvested daily, and stored at about 10° C. until emergence ceased, about 23 days post-inoculation. The treatment was then applied using a plastic spray bottle at a rate of about two infected *T. molitor*'s worth of Ijs per pot and evaluated 14 days later. The pots receiving the spray treatment were placed and evaluated along with other pots evaluated at 37 days post-inoculation. In each experiment, treatment effects were analyzed by sample date through ANOVA of mean percentage survival (transformed by arcsine of square root, alpha=0.05), and Tukey's multiple range test (SAS, SAS Software, Version 8e, SAS Institute, Cary, N.C., 1999).

Figure 2A:
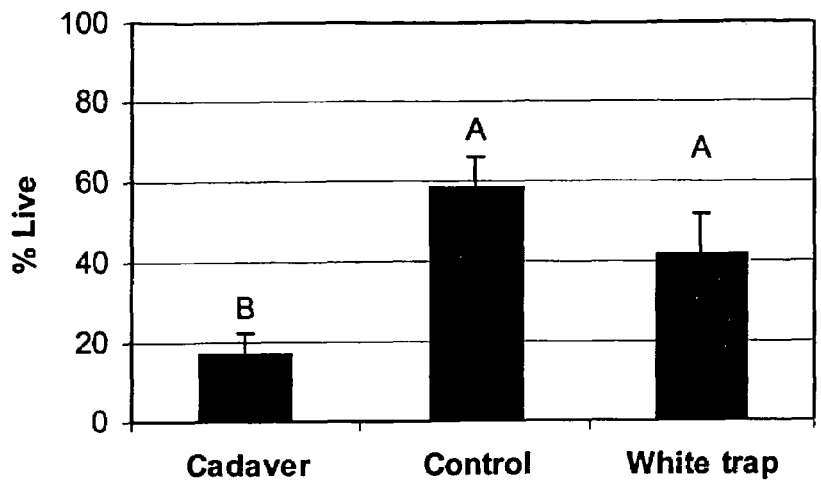
Figure 2B:
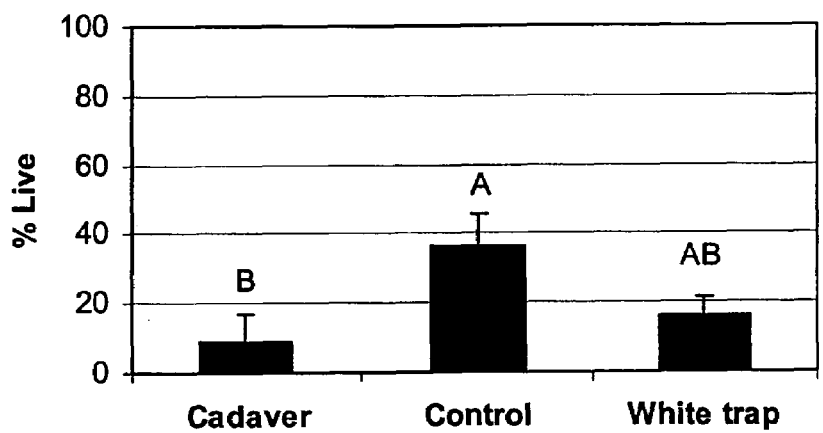
Figure 2C:
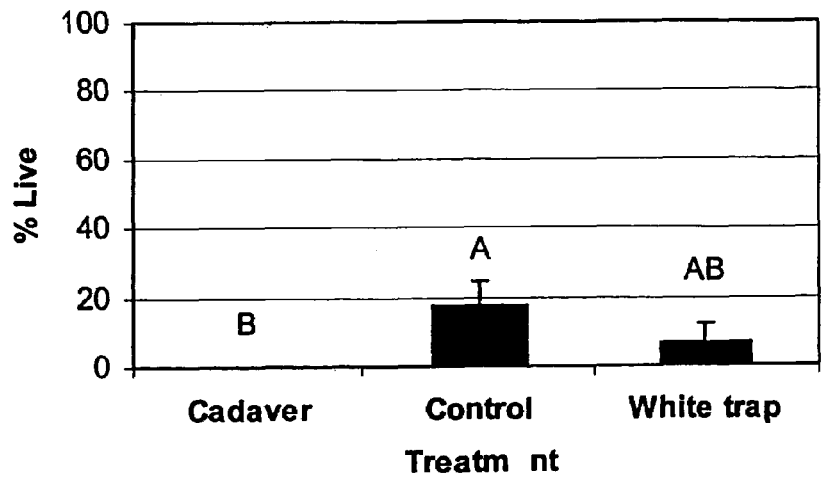

On all sample dates, survival of *D. abbreviatus* was lower in the infected cadaver treatment than the aqueous applications; all nematode applications caused reduced survival relative to untreated control (FIG. 1). With cadavers, no *D. abbreviatus* survival was observed in the last sample date. Aqueous application in spray versus White traps did not appear to affect efficacy (FIG. 1). With *O. sulcatus*, the cadaver treatment caused lower insect survival than the aqueous treatment in the first sample date, and was the only treatment causing lower survival than the control on all sample dates (FIG. 2). By the third sample date, control mortality reached high levels presumably due to age of the larvae or other unidentified natural mortality factors (FIG. 2). Several previous reports have suggested that efficacy of the cadaver application approach is approximately equal to application in aqueous, but these studies were inconclusive or flawed due to a complete lack of statistical methodology (Welch and Briand, Proc. Ent. Soc., Ont. Volume 91, 1970202, 1961), insufficient replication (Parkman et al., J. Entomol. Sci., Volume 28, 182-190, 1993), or a lack of power to show difference among treatments even between any treatment and the control (Jansson and Lecrone, Fla. Entomol., Volume 77, 281-284, 1994). The results of this study indicate that entomopathogenic nematode application in infected cadavers tends to be more efficacious than aqueous application. The increased efficacy observed in the cadaver applications may have been due to additional physiological stress in the aqueous application such as during temporary storage in water and upon application. Superior efficacy in the cadaver application might also have been due to compounds in the infected host cadaver that can enhance nematode infectivity or dispersal.

EXAMPLE 2

Figure 3:
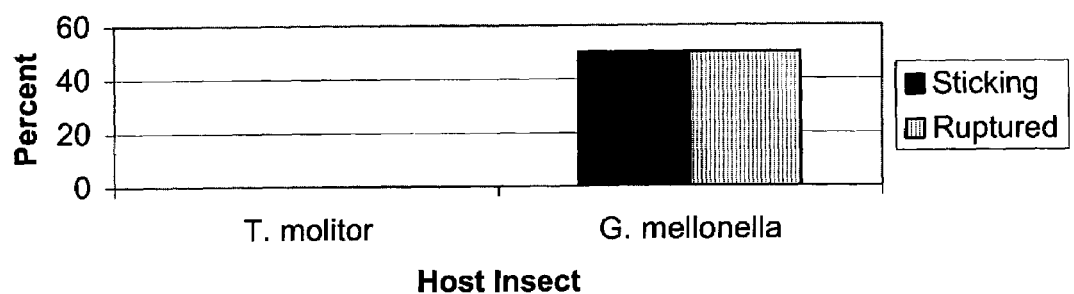

The tendency for the cadavers to rupture or stick together was evaluated in *Tenebrio molitor* and a soft-bodied host *Galleria mellonella* (greater waxmoth larva) seven days post-infection with the nematode *Heterorhabditis bacteriophora*. Four nematode infected cadavers of each host was placed in separate 90 mm petri dishes. The dishes were shook together three times for approximately 2 seconds each time and the order of the two dishes (top or bottom) was alternated between each shaking. The cadavers in separate petri dishes were then examined and the percentage ruptured and sticking together was recorded. In the Petri dish containing *G. mellonella*, about 50% of the cadavers ruptured and 50% stuck together whereas none of the *T. molitor* cadavers ruptured or stuck together (FIG. 3). This confirms that Tenebrio molitor infected hosts are more capable of withstanding stress than soft bodied hosts such as *Galleria mellonella*.

The foregoing detailed description is for the purpose of illustration. Such detail is solely for that purpose and those skilled in the art can make variations therein without departing from the spirit and scope of the invention.

What is claimed is:

1. A biocontrol composition comprising a pest reducing effective amount of a formulated nematode infected hard-bodied cadaver wherein said cadaver is from the family Tenebrionidae.

2. The composition of claim 1 wherein said cadaver is a *Tenebrio molitor* cadaver.

3. A method for reducing pests and/or microbials in agricultural, commercial, and urban environments comprising:
   (a) applying to an agricultural, commercial, or urban environment a formulated nematode infected hard-bodied cadaver wherein said cadaver is from the family Tenebrionidae in amounts effective to reduce pests and/or microbials in said environments.

4. The method of claim 3 wherein said cadaver is a *Tenebrio molitor* cadaver.

* * * * *